(12) United States Patent
Flannery et al.

(10) Patent No.: US 7,801,624 B1
(45) Date of Patent: Sep. 21, 2010

(54) REDUCED PERFORATION DISTAL TIP FOR AN IMPLANTABLE CARDIAC ELECTROTHERAPY LEAD

(75) Inventors: Conor Flannery, Santa Monica, CA (US); Virote Indravudh, Santa Clarita, CA (US); Phong D. Doan, Stevenson Ranch, CA (US); Diane Muff, Granada Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 761 days.

(21) Appl. No.: 11/623,667

(22) Filed: Jan. 16, 2007

(51) Int. Cl.
*A61N 1/00* (2006.01)
(52) U.S. Cl. ..................................... 607/116
(58) Field of Classification Search .................. 600/16, 600/486; 606/129; 607/116, 117, 119, 122, 607/126–129
See application file for complete search history.

(56) References Cited

U.S. PATENT DOCUMENTS

| | | | |
|---|---|---|---|
| 3,902,501 A * | 9/1975 | Citron et al. ................. | 607/126 |
| 5,003,992 A | 4/1991 | Holleman et al. | |
| 5,246,014 A | 9/1993 | Williams et al. | |
| 5,531,781 A * | 7/1996 | Alferness et al. ............ | 607/122 |
| 5,658,326 A | 8/1997 | Barsne | |
| 5,658,327 A | 8/1997 | Altman et al. | |
| 5,837,007 A | 11/1998 | Altman et al. | |
| 5,902,329 A | 5/1999 | Hoffmann et al. | |
| 6,901,288 B2 | 5/2005 | Janke et al. | |
| 2001/0044646 A1 * | 11/2001 | Marshall et al. ............. | 607/127 |
| 2003/0028224 A1 | 2/2003 | McVenes et al. | |
| 2004/0064172 A1 * | 4/2004 | McVenes et al. ............ | 607/122 |
| 2005/0070986 A1 * | 3/2005 | Tockman et al. ............ | 607/122 |
| 2005/0085885 A1 | 4/2005 | Janke et al. | |
| 2005/0175665 A1 | 8/2005 | Hunter et al. | |
| 2005/0175703 A1 | 8/2005 | Hunter et al. | |
| 2005/0178395 A1 | 8/2005 | Hunter et al. | |
| 2005/0178396 A1 | 8/2005 | Hunter et al. | |
| 2005/0186244 A1 | 8/2005 | Hunter et al. | |
| 2005/0187140 A1 | 8/2005 | Hunter et al. | |
| 2005/0196421 A1 | 9/2005 | Hunter et al. | |
| 2005/0208095 A1 | 9/2005 | Hunter et al. | |
| 2006/0247753 A1 * | 11/2006 | Wenger et al. ............... | 607/126 |
| 2007/0043414 A1 * | 2/2007 | Fifer et al. ................... | 607/126 |
| 2007/0050003 A1 | 3/2007 | Zarembo et al. | |
| 2008/0097567 A1 * | 4/2008 | Haldeman .................... | 607/128 |
| 2008/0103576 A1 * | 5/2008 | Gerber ......................... | 607/128 |

FOREIGN PATENT DOCUMENTS

| | | |
|---|---|---|
| EP | 0618822 B1 | 1/1997 |
| EP | 0761254 B1 | 11/2003 |
| WO | WO 2005/051316 A2 | 6/2005 |
| WO | WO 2005/051452 A2 | 6/2005 |

OTHER PUBLICATIONS

Khan, Mohammed N. et al, "Delayed Lead Perforation: A Disturbing Trend," PACE 2005;28:251-253.

* cited by examiner

*Primary Examiner*—George Manuel
*Assistant Examiner*—Robert N Wieland

(57) ABSTRACT

An implantable cardiac electrotherapy lead is disclosed herein. In one embodiment, the lead includes a tubular body having a distal end with a first soft resilient member. The member extends or is extendable from the distal end radially outward relative to a longitudinal axis of the tubular body.

37 Claims, 14 Drawing Sheets

REDUCED PERFORATION DISTAL TIP FOR AN IMPLANTABLE CARDIAC ELECTROTHERAPY LEAD

FIELD OF THE INVENTION

The present invention relates to medical apparatus and methods. More specifically, the present invention relates to implantable cardiac electrotherapy leads and methods of using such leads.

BACKGROUND OF THE INVENTION

Cardiac electrotherapy leads are implanted within various locations of a heart to provide pacing and/or defibrillation electrotherapy. Cardiac perforation of the right ventricle ("RV") wall is a risk associated with all transvenous lead implantations to the RV apical site, especially active fixation leads, leads with smaller diameters, and defibrillation leads. The likelihood of perforation is a function of the lead and/or stylet configuration and the dexterity of the implanting surgeon.

In rare cases, the distal end of a lead acts as a spear that pierces the RV wall, either during implantation of the lead or in the succeeding months. If a lead perforates the myocardium, acute patient symptoms can include pericardial effusion, cardiac tamponade, pericarditis, or even death. Additionally, a lead that has perforated the myocardium may be non-functioning and may cause chest pain or pneumothorax.

The RV apical wall can be as thin as one millimeter thick, and the right atrium ("RA") appendage can be less than one millimeter thick. In contrast, a helix extending from the distal tip of a lead can be two millimeters long when fully extended. As a result, it is possible for the helix to cross the entire thickness of a RV apical wall or a RA appendage wall.

There is a need in the art for an implantable cardiac electrotherapy lead configured to reduce the likelihood of cardiac perforation. There is also a need in the art for a method of making and deploying such a lead.

BRIEF SUMMARY

An implantable cardiac electrotherapy lead is disclosed herein. In one embodiment, the lead includes a tubular body having a distal end with a first soft resilient member. The member extends or is extendable from the distal end radially outward relative to a longitudinal axis of the tubular body.

An implantable cardiac electrotherapy lead is disclosed herein. In one embodiment, the lead includes a tubular body having a distal end with first and second members. The members are extendable from the distal end radially outward relative to a longitudinal axis of the tubular body.

A method of implanting an implantable cardiac electrotherapy lead is disclosed herein. In one embodiment, the method includes distally passing a distal end of the lead through an introducer sheath when the distal end has a reduced diameter, and expanding the diameter of the distal end upon exiting a distal end of the introducer sheath with the distal end of the lead.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1A:
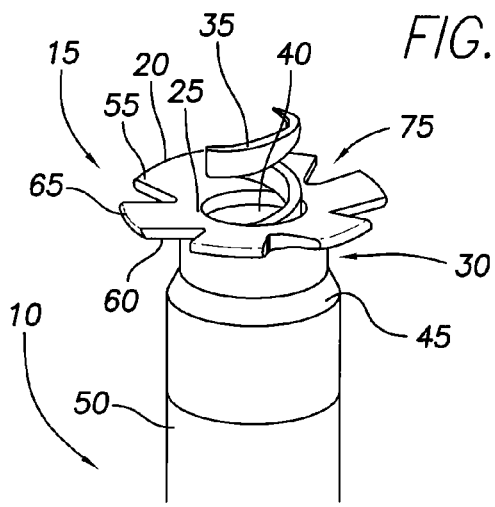
FIG. 1A is an isometric view of one embodiment of the distal end of a lead tubular body having members radially outwardly extending from the distal end.

The present application describes tubular body 10 of an implantable cardiac electrotherapy lead (e.g., a bradycardia lead, tachycardia lead, or etc.). The lead tubular body 10 has a distal end 15 configured to reduce the likelihood of myocardial perforation when the lead distal end 15 contacts a myocardial surface during the implantation of the lead within the heart of a patient. In some embodiments, the lead tubular body 10 includes a distal end 15 that has a modifiable diameter that can be increased as the distal end 15 approaches a myocardial surface. In some embodiments, the lead tubular body 10 includes a distal end 15 that provides a soft material interface for contacting the myocardial surface. In some embodiments, the lead tubular body 10 includes a distal end 15 having resistance features that provide resistance to the distal end 15 penetrating the myocardial surface. In some embodiments, the lead tubular body 10 includes a distal end 15 employing any two or more of the aforementioned techniques for reducing the likelihood of the distal end 15 perforating a myocardial surface.

For a discussion regarding various embodiments of the lead tubular body 10 employing a cushioning distal end 15 with a modifiable diameter, reference is made to FIGS. 1A-3B. FIGS. 1A-3B are isometric views of various embodiments of the distal end 15 of a lead tubular body 10 having members 20 radially outwardly extending from the distal end 15. As shown in FIGS. 1A-3B, the distal end 15 of the lead tubular body 10 includes one or more radially outwardly extending members 20, a distal end face 25, a recess 30 or pocket 32, a helix 35, a helix lumen 40, a bevel 45 or lip 47, and an outer circumferential surface 50.

As can be understood from FIGS. 1A-3B, the outer circumferential surface 50 extends proximally from the distal end 15 generally uniformly to define the surface of the lead tubular body 10. The helix 35 serves as a mechanism for fixing the lead distal end 15 to a myocardial surface. The helix 35 is distally/proximally displaceable within the helix lumen 40 to extend or retract the helix 35 within the lumen 40. The distal end face 25 extends about the lumen 40 and forms the most distal surface of the lead tubular body 10.

As illustrated in FIGS. 1A-3B, the members 20 extend radially outwardly from the distal end 15 and include a distal face 55, a proximal face 60 and an outer edge or rim 65. As indicated in FIGS. 1A, 1B, 2A, 2D, and 3B, each member 20 is positioned on the distal end 15 such that the member distal face 55 radially outwardly extends from the distal end face 25 of the lead tubular body 10 as a continuous uninterrupted surface to the member outer rim 65. Alternatively, as depicted in FIGS. 2B, 2C, 2E and 3A, each member 20 is positioned on the distal end 15 such that the member distal face 55 radially outwardly extends from the distal end 15 at a point proximally offset a small distance from the distal end face 25, thereby defining a rim or lip 70 extending circumferentially about, and generally perpendicularly to, the distal end face 25.

As can be understood from FIGS. 1A, 1B, 3A and 3B, in various embodiments, the tubular body outer circumferential surface 50 extends generally uniformly distally from the tubular body proximal end until reaching the bevel 45 where the diameter of the lead tubular body 10 transitions to a smaller diameter to form the recess 30. The recess 30 is defined between the proximal face(s) 60 of the member(s) 20 and the bevel 45. The recess 30 and bevel 45 extend about the circumference of the lead tubular body 10.

In various alternative embodiments, as can be understood from FIGS. 2A-2E, the tubular body outer circumferential surface 50 extends generally uniformly distally from the tubular body proximal end until nearing the vicinity of the members 20 where lips 47 define pockets 32 in the tubular body outer circumferential surface 50. In one embodiment, each pocket 32 aligns with and matches the shape and size of its corresponding member 20.

As can be understood from FIGS. 1A-3B, the members 20 are resiliently flexible and formed from a polymer material such as silicone rubber, polyurethane, silicone-polyurethane-copolymer ("SPC"), or etc. Thus, when the lead tubular body 10 is distally extended through an introducer sheath, the members 20 deflect proximally to reside within the recess 30 or seat within the corresponding pocket 32, as the case may be, to allow the diameter of the lead distal end 15 to reduce to generally match the diameter of the rest of the lead tubular body 10. As a result, the lead tubular body 10 can pass through an introducer sheath sized for the passage of a typical lead. Once the lead distal end 15 emerges from the distal end of the introducer sheath, the members are free to radially outwardly extend from the recess 30 or their respective pockets 32. Thus, the lead tubular body 10 is advantageous because it can be deployed via a typically sized introducer sheath while providing a distal end 15 with a substantially enlarged diameter to reduce the likelihood of myocardial perforation by the lead tubular body 10 when being implanted.

Figure 1B:
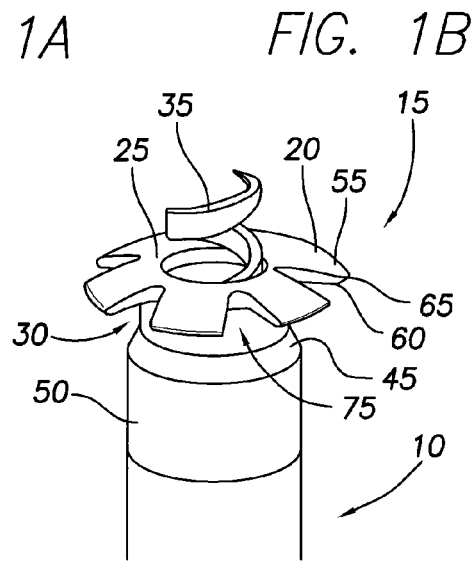
FIG. 1B is an isometric view of one embodiment of the distal end of a lead tubular body having members radially outwardly extending from the distal end.
Figure 2B:
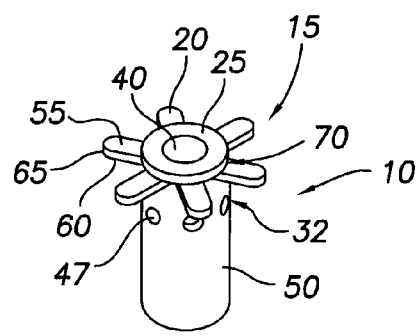
FIG. 2B is an isometric view of one embodiment of the distal end of a lead tubular body having members radially outwardly extending from the distal end.
Figure 2D:
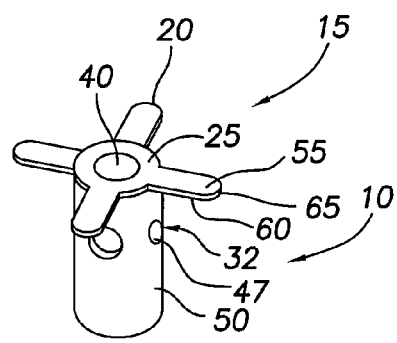
FIG. 2D is an isometric view of one embodiment of the distal end of a lead tubular body having members radially outwardly extending from the distal end.
Figure 2A:
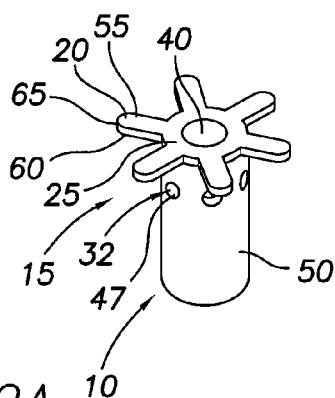
FIG. 2A is an isometric view of one embodiment of the distal end of a lead tubular body having members radially outwardly extending from the distal end.
Figure 2C:
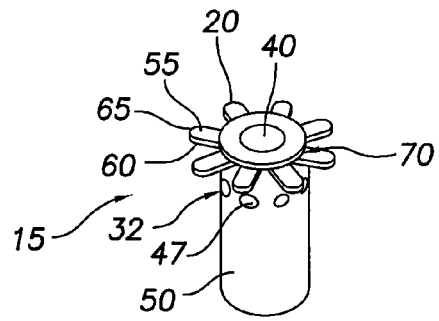
FIG. 2C is an isometric view of one embodiment of the distal end of a lead tubular body having members radially outwardly extending from the distal end.
Figure 2E:
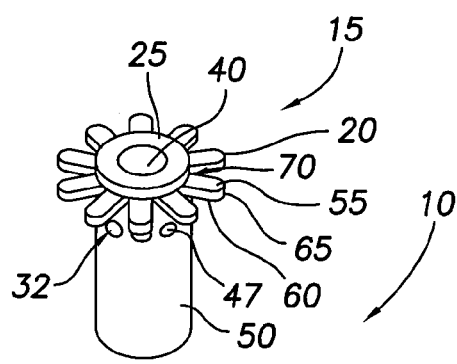
FIG. 2E is an isometric view of one embodiment of the distal end of a lead tubular body having members radially outwardly extending from the distal end.

As shown in FIGS. 1A and 1B, in various embodiments, the members 20 are generally rectangular and separated by V-shaped gaps 75. The members 20 taper as they extend towards their outer rim 65. As indicated in FIG. 1A, in one embodiment, the members 20 are concave in orientation such that the members 20 curve slightly distally. As illustrated in FIG. 1B, in one embodiment, the members 20 are convex in orientation such that the members 20 curve slightly proximally.

As illustrated in FIGS. 2A-2E, in various embodiments, the members 20 are generally elongated, radiate outwardly from the outer circumferential surface 50 of the tubular body 10, terminate with arcuate shaped outer rims 65, and are generally uniform in thickness along their entire lengths. The corresponding pockets 32 are similarly shaped and arranged to accept the members 20.

Figure 3A:
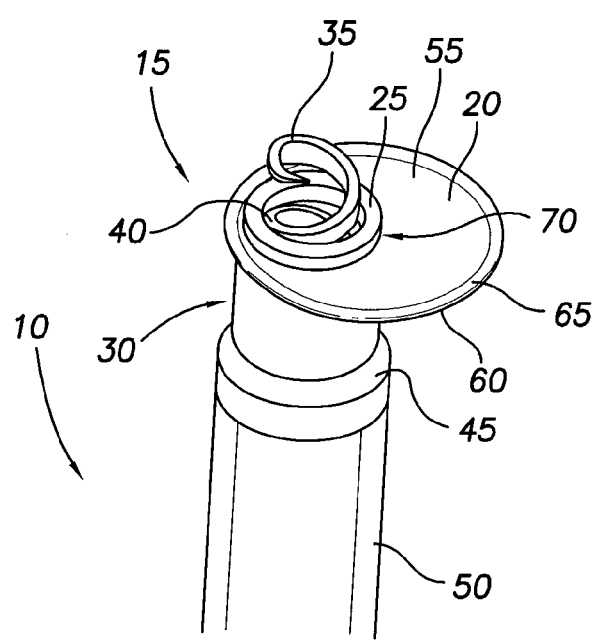
FIG. 3A is an isometric view of one embodiment of the distal end of a lead tubular body having a member radially outwardly extending from the distal end.
Figure 3B:
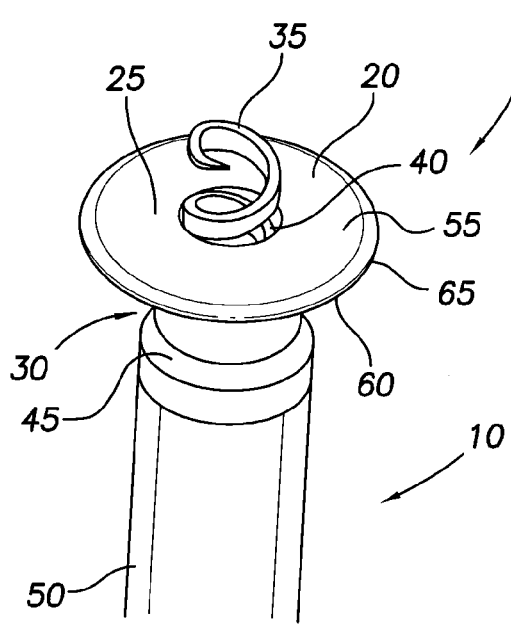
FIG. 3B is an isometric view of one embodiment of the distal end of a lead tubular body having a member radially outwardly extending from the distal end.

As indicated in FIGS. 3A-3B, in various embodiments, the member 20 will be a generally continuous circular disk 20 radially outwardly extending from the distal end 15. In one embodiment, as shown in FIG. 3B, the circular disk member 20 is concentric with the tubular body 10 in that the member 20 is centered about the lumen 40. In another embodiment, circular disk member 20 is eccentric with the tubular body 10 in that the center of the circular disk member 20 is offset from the lumen 40.

As can be understood from FIGS. 1A-3B, depending on the embodiment, the distal end 15 can have any number of members 20 radially extending from the distal end 15. Ultimately, in each of the embodiments depicted in FIGS. 1A-3B, the members 20 radially outwardly extend from the distal end 15 to create an enlarged deflectable footprint that reduces the likelihood of myocardial perforation by the distal end 15. Additionally, the members 20 fold proximally, thereby allowing the lead tubular body 10 to be deployed through a typically sized introducer sheath.

For a discussion regarding various other embodiments of the lead tubular body 10 employing a cushioning distal end 15 with a modifiable diameter, reference is made to FIGS. 4A-6B. FIGS. 4A-6B are isometric and sectional views of various embodiments of the distal end 15 of a lead tubular body 10 having a member or sleeve 20 that is radially outwardly expandable from the distal end 15. As shown in FIGS. 4A-6B, the distal end 15 of the lead tubular body 10 includes a radially outwardly expandable sleeve 20, a distal end face 25, a helix 35, a helix lumen 40, and an outer circumferential surface 50.

As can be understood from FIGS. 4A-6B, the outer circumferential surface 50 extends proximally from the distal end 15 generally uniformly to define the surface of the lead tubular body 10. The helix 35 serves as a mechanism for fixing the lead distal end 15 to a myocardial surface. The helix 35 is distally/proximally displaceable within the helix lumen 40 to extend or retract the helix 35 within the lumen 40. The distal end face 25 extends about the lumen 40 and forms the most distal surface of the lead tubular body 10.

Figure 4A:
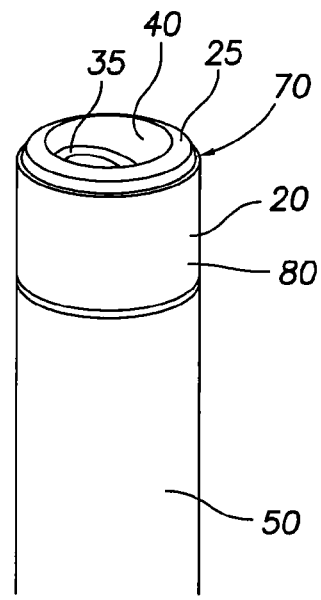
FIG. 4A is an isometric view of one embodiment of the distal end of a lead tubular body having a radially outwardly expandable sleeve in a non-expanded state.
Figure 5A:
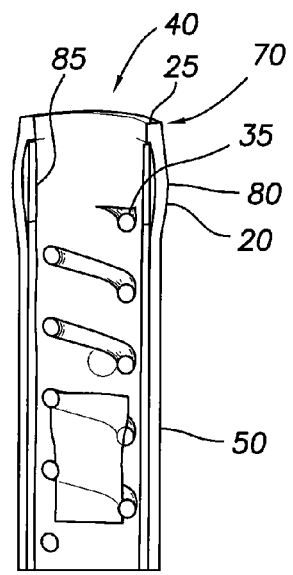
FIG. 5A is a sectional view of one embodiment of the distal end of a lead tubular body having a radially outwardly expandable sleeve in a non-expanded state.
Figure 6A:
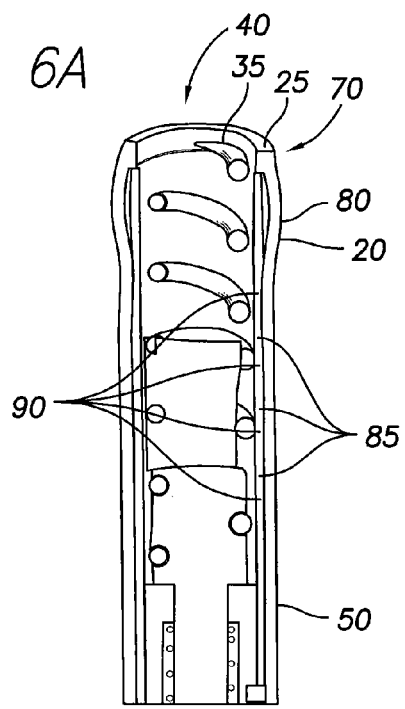
FIG. 6A is a sectional view of one embodiment of the distal end of a lead tubular body having a radially outwardly expandable sleeve in a non-expanded state.

As shown in FIGS. 4A, 5A and 6A, when the member or sleeve 20 is in its non-deployed or non-expanded state, the outer circumferential surface 80 of the sleeve 20 is generally continuously uniform or flat with the outer circumferential surface 50 of the lead tubular body 10. In other words, when in its non-expanded state, the diameter of the member or sleeve 20 is generally the same as the diameter of the rest of the lead tubular body 10.

Figure 4B:
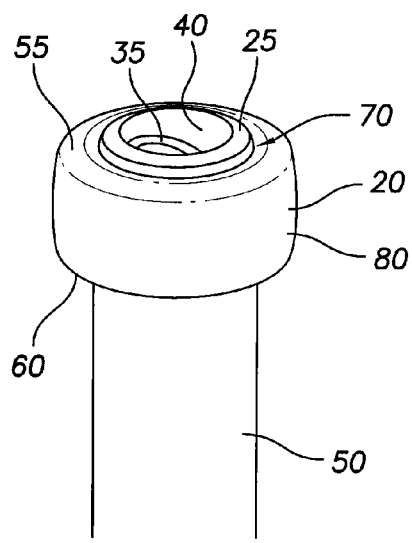
FIG. 4B is an isometric view of one embodiment of the distal end of a lead tubular body having a radially outwardly expandable sleeve in an expanded state.
Figure 5B:
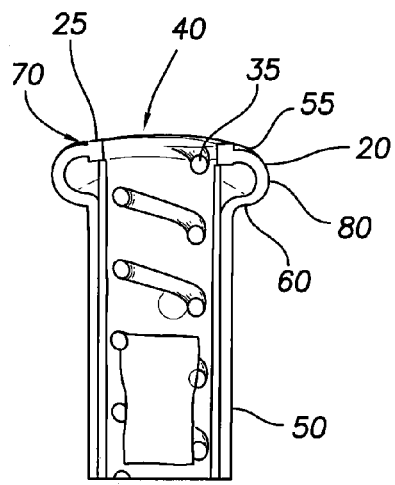
FIG. 5B is a sectional view of one embodiment of the distal end of a lead tubular body having a radially outwardly expandable sleeve in an expanded state.
Figure 6B:
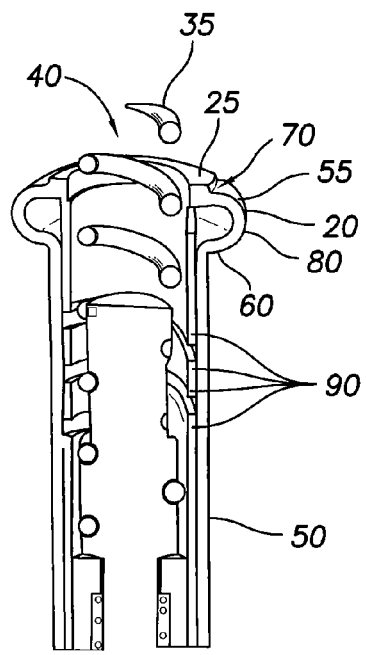
FIG. 6B is a sectional view of one embodiment of the distal end of a lead tubular body having a radially outwardly expandable sleeve in an expanded state.

As indicated in FIGS. 4B, 5B and 6B, when the member or sleeve 20 is in its deployed or expanded state, the outer circumferential surface 80 of the sleeve 20 expands outwardly from its non-expanded state, thereby increasing the diameter of the distal end 15 across the expanded member 20. In its expanded state, the sleeve 20 has a distal face 55 and a proximal face 60. In one embodiment, the sleeve 20 is positioned on the distal end 15 such that the sleeve distal face 55 radially outwardly extends from the distal end 15 at a point proximally offset a small distance from the distal end face 25, thereby defining a rim or lip 70 extending circumferentially about, and generally perpendicularly to, the distal end face 25.

As can be understood from FIGS. 4A and 4B, in one embodiment, a ring of swellable material is located below the surface of the member or sleeve 20, which is made of a resilient polymer such as silicone rubber, polyurethane, SPC, or etc. The swellable material is activated or caused to swell by exposure to a biological fluid. In one embodiment, the swellable material is a silicone, poly-vinyl alcohol ("PVA") hydrogel, or other swellable material molded into a ring with the inner diameter of the member 20.

The lead tubular body 10 is distally passed through an introducer sheath in its non-expanded state so the lead tubular body 10 can pass through a typically sized introducer sheath without resistance. Once the lead distal end 15 exits the distal end of the introducer sheath and is exposed to biological fluid, the swellable material swells and the member or sleeve 20 expands from its non-expanded state (FIG. 4A) to its expanded state (FIG. 4B). As a result, the footprint of the distal end 15 of the lead tubular body 10 increases, and the likelihood of myocardial perforation by the distal end 15 is reduced.

In one embodiment, the molded ring can swell to a larger outer diameter due to an impregnated swelling agent such as a steroid. Dexamethasone ("DexA") and dexamethasone sodium phosphate ("DSP") can swell approximately 10% and 35% by diameter, respectively. The use of a steroid as the swelling agent may also provide therapy to reduce inflammation of the surrounding tissue.

As can be understood from FIGS. 5A and 5B, in one embodiment, the member 20 is a sleeve made of a preformed polymer material such as silicone rubber, polyurethane, SPC, or etc. As shown in FIG. 5A, the preformed member or sleeve 20 is maintained in the non-deployed or non-expanded state via a dissolvable cylinder 85 that is used to keep the preformed sleeve 20 stretched out flat to be of a generally uniform diameter with the rest of the outer circumferential surface 50 of the lead tubular body 10. The lead tubular body 10 distally passes through an introducer sheath in its non-expanded state (FIG. 5A). Once the lead distal end 15 exits the distal end of the introducer sheath and is exposed to biological fluid (e.g., blood), the dissolvable cylinder 85 begins to dissolve. Once the dissolvable cylinder 85 is sufficiently dissolved, the preformed sleeve 20 is free to assume its preformed expanded configuration (FIG. 5B), thereby increasing the footprint of the lead distal end 15 and reducing the likelihood of myocardial perforation by the lead distal end 15.

In one embodiment, the dissolvable cylinder 85 is formed of Mannitol, a slightly sweet alcohol, $C_6H_8(OH)_6$, which dissolves in approximately three to five minutes. In other embodiments, the cylinder 85 is formed of other dissolvable materials.

In one embodiment, which is depicted in FIGS. 6A and 6B and is similar to that discussed with respect to FIGS. 5A and 5B, the dissolvable cylinder 85 is a helical spacer 85 helically positioned between a helical header component 90. The helical header component 90 is a flat wire 90 that is maintained in a stretch/extended state by the coils 85 of the dissolvable helical spacer 85, which are positioned between the coils 90 of the helical flat wire 90. When the helical flat wire 90 is maintained in the extended state by the dissolvable spacer 85, the preformed sleeve 20 is maintained in its non-deployed or non-expanded state such that is diameter generally conforms to the diameter of the rest of the lead tubular body 10. Once the dissolvable spacer 85 is exposed to biological fluid, the spacer eventually dissolves and no longer maintains the helical flat wire 90 in an extended state. In other words, the helical flat wire 90 is free to return to its natural length. As a result, the preformed sleeve 20 is free to expand to the deployed state, thereby increasing the footprint of the lead distal end 15 and reducing the likelihood of myocardial perforation by the lead distal end 15.

Figure 7A:
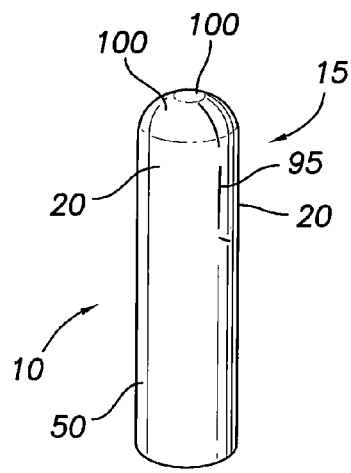
FIG. 7A is an isometric view of one embodiment of the distal end of a lead tubular body having radially outwardly expandable members in a closed non-expanded configuration.
Figure 7B:
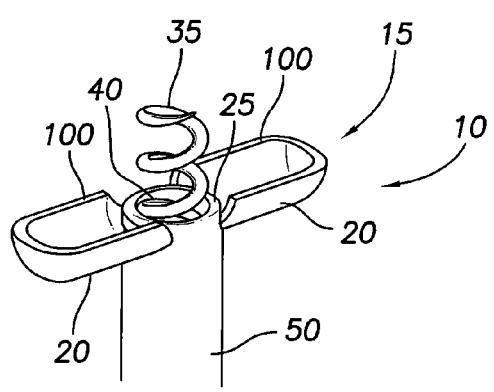
FIG. 7B is an isometric view of one embodiment of the distal end of a lead tubular body having radially outwardly expandable members in an open expanded configuration.

For a discussion regarding another embodiment of the lead tubular body 10 employing a cushioning distal end 15 with a modifiable diameter, reference is made to FIGS. 7A-7B. FIGS. 7A-7B are isometric views of various embodiments of the distal end 15 of a lead tubular body 10 having members or helix covers 20 that are radially outwardly expandable from the distal end 15. As shown in FIGS. 7A-7B, the distal end 15 of the lead tubular body 10 includes covers 20 that can be opened into a radially outwardly expanded configuration, a distal end face 25, a helix 35, a helix lumen 40, and an outer circumferential surface 50.

As can be understood from FIGS. 7A-7B, the outer circumferential surface 50 extends proximally from the distal end 15 generally uniformly to define the surface of the lead tubular body 10. The helix 35 serves as a mechanism for fixing the lead distal end 15 to a myocardial surface. The helix 35 is distally/proximally displaceable within the helix lumen 40 to extend or retract the helix 35 within the lumen 40.

As can be understood from FIGS. 7A and 7B, the members or helix covers 20 pivot from a closed longitudinally extending configuration to an opened radially outwardly extended configuration. As shown in FIG. 7A, when in the non-deployed or non-expanded configuration, the covers 20 reside in a longitudinally extending position where the covers 20 are closed against each other in an opposed fashion along a seam 95. The extreme distal ends 100 of the covers 20 are arcuate and form the extreme distal end of the lead tubular body 10 when the covers 20 are in the non-deployed configuration. In one embodiment, the covers 20 are shell-like and, when in the non-deployed configuration, enclose the helix 35 and form a circumferential surface with a diameter that generally matches the diameter of the outer circumferential surface 50 of the lead tubular body 10.

In one embodiment, although the covers 20 are shell-like and can enclose the helix 35, the helix 35 remains retracted within the tubular body 10 proximal of the distal end face 25 until the covers 20 are opened in anticipation of helix deployment. Upon opening the covers 20, the helix 35 is distally displaced to extend distally past the distal end face 25. The helix 35 is then anchored in the heart tissue for implantation of the lead tubular body 10.

The members or covers 20 are hinged to the rest of the tubular body 10 and are biased to open into the deployed or expanded configuration illustrated in FIG. 7B. The implanting physician closes the covers 20 together into the non-deployed configuration and inserts the lead distal end 15 into the proximal end of an introducer sheath. The lead tubular body 10 is distally passed through the introducer sheath in the non-deployed configuration. When the distal end 15 of the lead tubular body 10 exits the distal end of the introducer sheath, the covers 20 bias into the deployed configuration depicted in FIG. 7B.

As illustrated in FIG. 7B, in one embodiment, when the members or covers 20 bias into the open, deployed configuration, the covers 20 are approximately 180 degrees apart. Each cover 20 includes seam faces 100 that generally align with the distal face 25 of the lead tubular body 10 when in the deployed configuration. Thus, the seam faces 100 and the distal end face 25, which extends about the lumen 40, combine to form the most distal surface of the lead tubular body 10.

As can be understood from FIG. 7A, when the members or covers 20 close together in the non-deployed configuration, the seam faces 100 abut to form the seam 95. While in the non-deployed configuration, the arcuate distal ends 100 of the covers 20 form the most distal end of the lead tubular body 10.

In one embodiment, the shell-like members or covers 20 are formed from a polymer material such as silicone rubber, polyurethane, SPC, or etc. In other embodiments, the covers 20 are formed in generally the same manner as the rest of the lead tubular body 10.

As can be understood from FIGS. 7A and 7B, when the members or covers 20 are in the closed, non-deployed configuration, the lead tubular body 10 can pass through a typically sized introducer sheath. When the covers 20 are in the open, deployed configuration, the footprint of the lead distal end 15 is increased, thereby reducing the likelihood of myocardial perforation by the lead distal end 15.

Figure 8A:
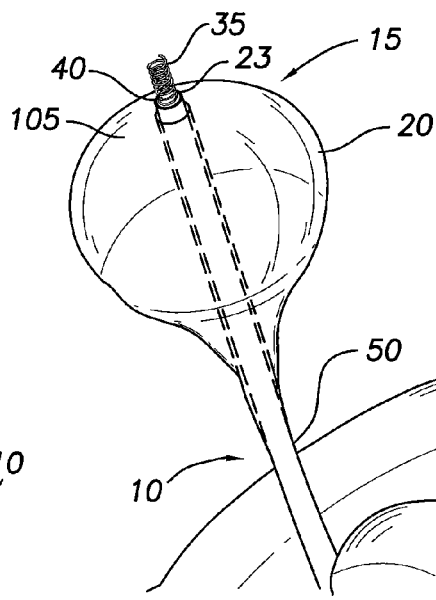
FIG. 8A is an isometric view of one embodiment of the distal end of a lead tubular body having a radially outwardly expandable balloon in an expanded configuration.
Figure 8B:
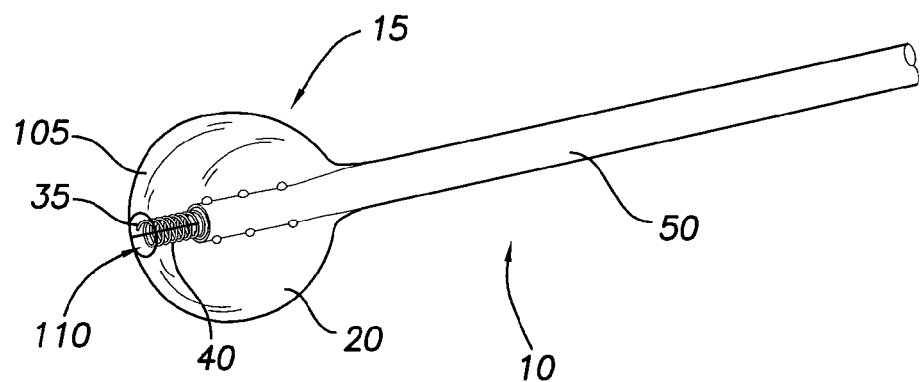
FIG. 8B is a side view of one embodiment of the distal end of a lead tubular body having a radially outwardly expandable balloon in an expanded configuration.

For a discussion regarding another embodiment of the lead tubular body 10 employing a cushioning distal end 15 with a modifiable diameter, reference is made to FIGS. 8A-8B. FIGS. 8A-8B are, respectively, an isometric view and a side view of various embodiments of the distal end 15 of a lead tubular body 10 having a member or balloon 20 that is radially outwardly expandable from the distal end 15. As shown in FIGS. 8A-8B, the distal end 15 of the lead tubular body 10 includes a member or balloon 20 that can be inflated into a radially outwardly expanded configuration, a helix 35, a helix lumen 40, and an outer circumferential surface 50.

As can be understood from FIGS. 8A and 8B, the lead tubular body 10 distally travels through an introducer sheath when the balloon 20 is in an un-inflated or non-expanded state. When in the un-inflated state, the balloon 20 does not substantially exceed the diameter of the rest of the lead tubular body 10 and, as a result, the lead tubular body 10 is able to pass unimpeded through a typically sized introducer sheath.

Once the lead distal end 15 exits the introducer distal end, the balloon 20 can be inflated via a fluid (e.g., compressed air, carbon dioxide, saline, etc.) to assume the expanded or deployed state, as depicted in FIGS. 8A and 8B. The balloon 20 is inflated via a fluid supply (e.g., a pump) in fluid communication with the balloon 20 via one or more fluid conveying lumens extending the length of the lead tubular body 10. In the inflated or expanded state, the balloon 20 increases the footprint of the lead distal end 15 and creates a cushion, thereby reducing the likelihood of the lead distal end 15 perforating the myocardial surface.

In one embodiment, the balloon 20 is formed of polymer materials such as polyethylene terephthalate ("PET"), latex rubber, silicone rubber, or other expandable polymers.

As indicated in FIGS. 8A and 8B, in various embodiments, the balloon 20 is pear or spherically shaped. As shown in FIG. 8A, in one embodiment, the distal surface 105 of the balloon 20 is located at or slightly proximal to the distal end surface 25 of the lead tubular body 10. In one embodiment, the distal surface 105 of the balloon 20 is located slightly distal of the distal end surface 25 of the lead tubular body 10. A lumen 110 defined in the balloon 20 coaxially aligns with, and extends down to, the helix lumen 40 to provide a path for the extension of the helix 35 into the myocardial surface.

For a discussion regarding various embodiments of the lead tubular body 10 employing a cushioning distal end 15 with a modifiable diameter, reference is made to FIGS. 9A-12B. FIGS. 9A-12B are isometric and sectional views of various embodiments of the distal end 15 of a lead tubular body 10 having members 20, 115 radially outwardly and inwardly extending from the distal end 15. As shown in FIGS. 9A-12B, the distal end 15 of the lead tubular body 10 includes one or more radially outwardly extending members 20, a radially inwardly extending member or flange 115, a distal end face 25, a helix 35, a helix lumen 40, a bevel 45 or lip 47, and an outer circumferential surface 50. In some embodiments, as depicted in FIGS. 10A and 10B, the distal end 15 also includes a recess 30.

As can be understood from FIGS. 9A-12B, the outer circumferential surface 50 extends proximally from the distal end 15 generally uniformly to define the surface of the lead tubular body 10. The helix 35 serves as a mechanism for fixing the lead distal end 15 to a myocardial surface. The helix 35 is distally/proximally displaceable within the helix lumen 40 to extend or retract the helix 35 within the lumen 40. The distal end face 25 extends about the lumen 40 and forms the most distal surface of the lead tubular body 10.

Figure 10A:
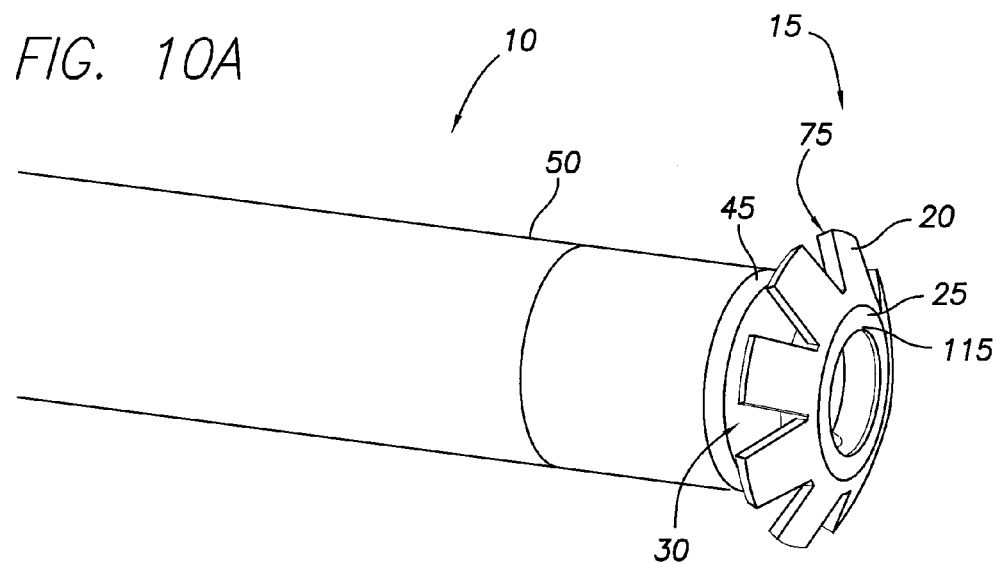
FIG. 10A is an isometric view of one embodiment of the distal end of a lead tubular body having members radially inwardly and outwardly extending from the distal end.
Figure 10B:
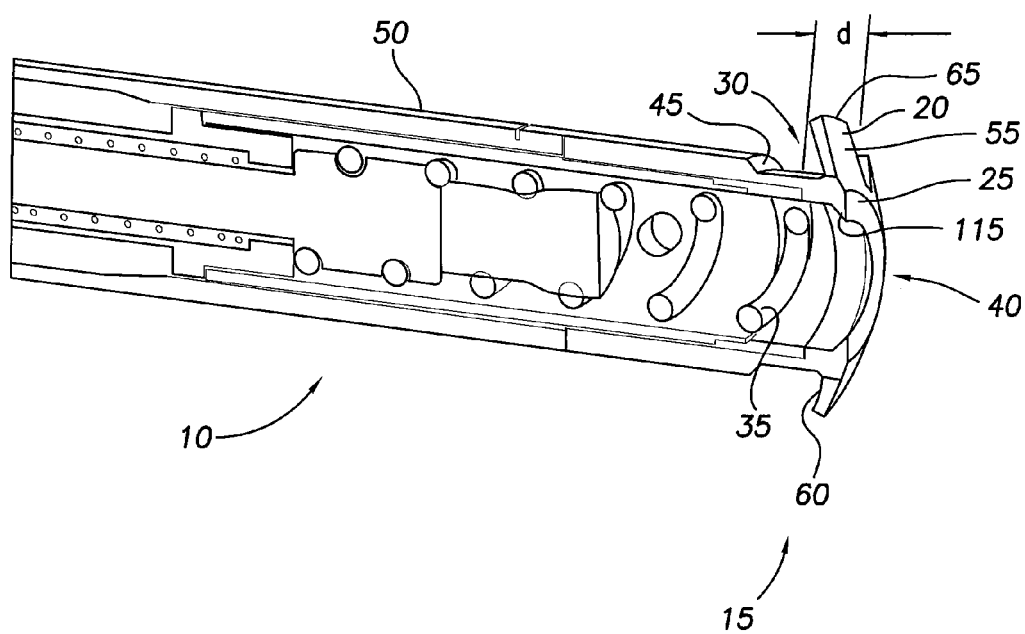
FIG. 10B is a sectional of view one embodiment of the distal end of a lead tubular body having members radially inwardly and outwardly extending from the distal end.
Figure 11A:
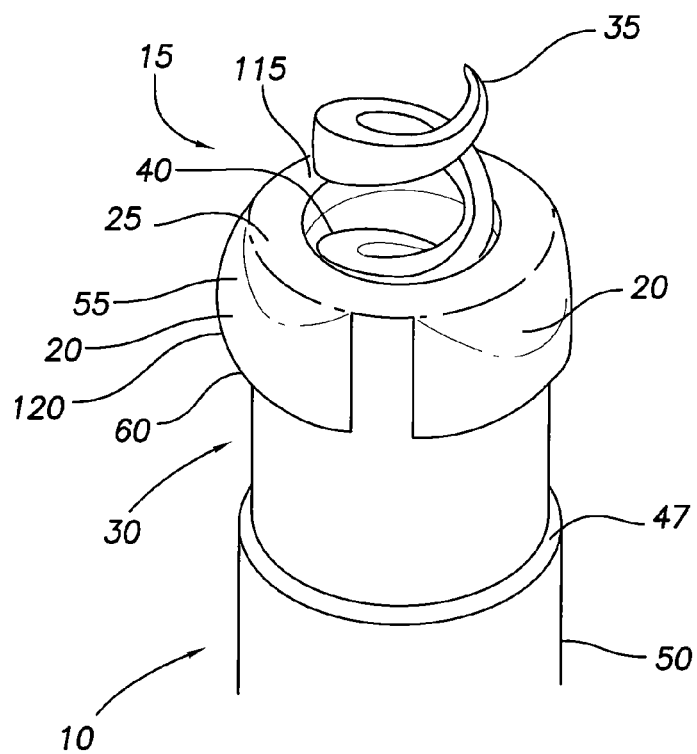
FIG. 11A is an isometric view of one embodiment of the distal end of a lead tubular body having members radially inwardly and outwardly extending from the distal end.
Figure 11B:
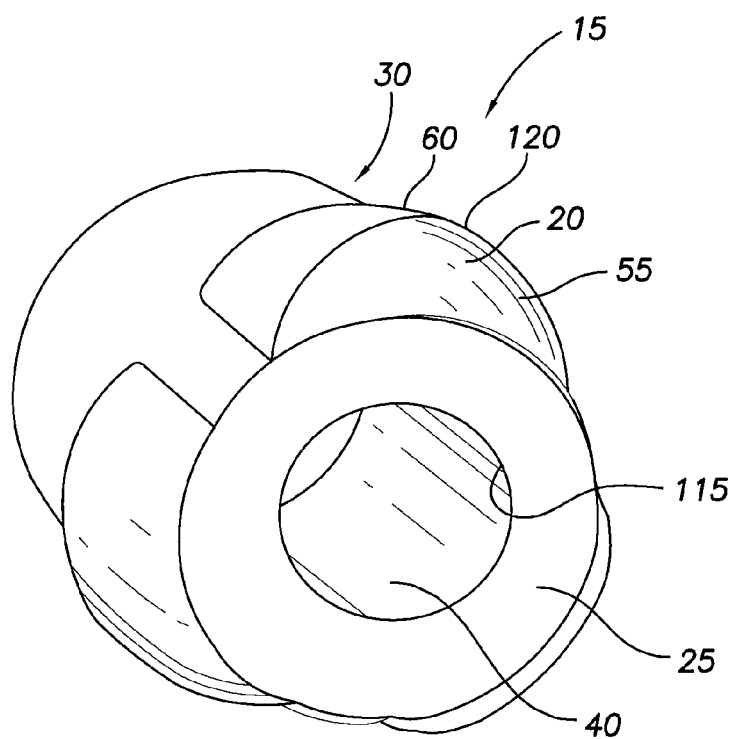
FIG. 11B is an isometric view of one embodiment of the distal end of a lead tubular body having members radially inwardly and outwardly extending from the distal end.
Figure 12A:
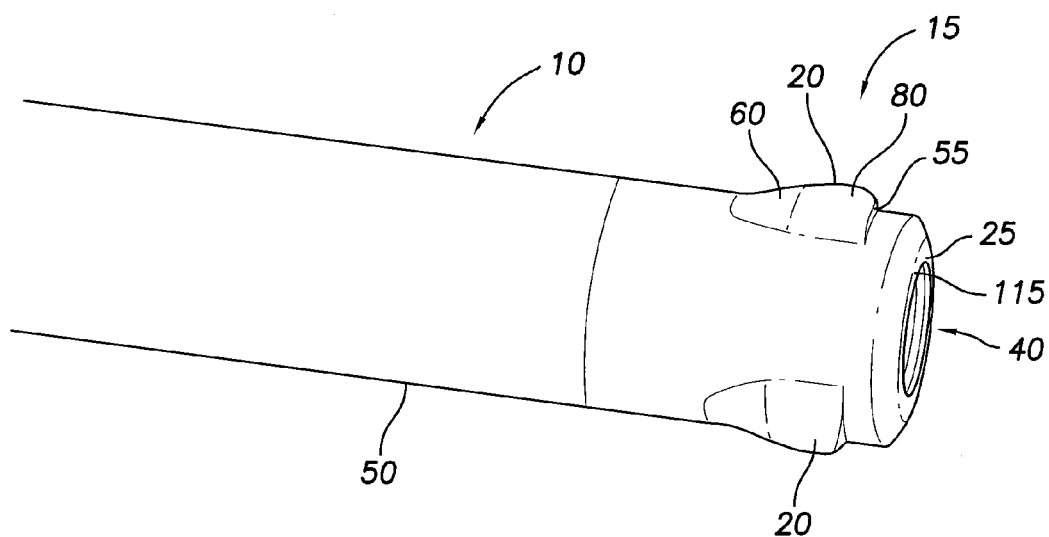
FIG. 12A is an isometric view of one embodiment of the distal end of a lead tubular body having members radially inwardly and outwardly extending from the distal end.
Figure 12B:
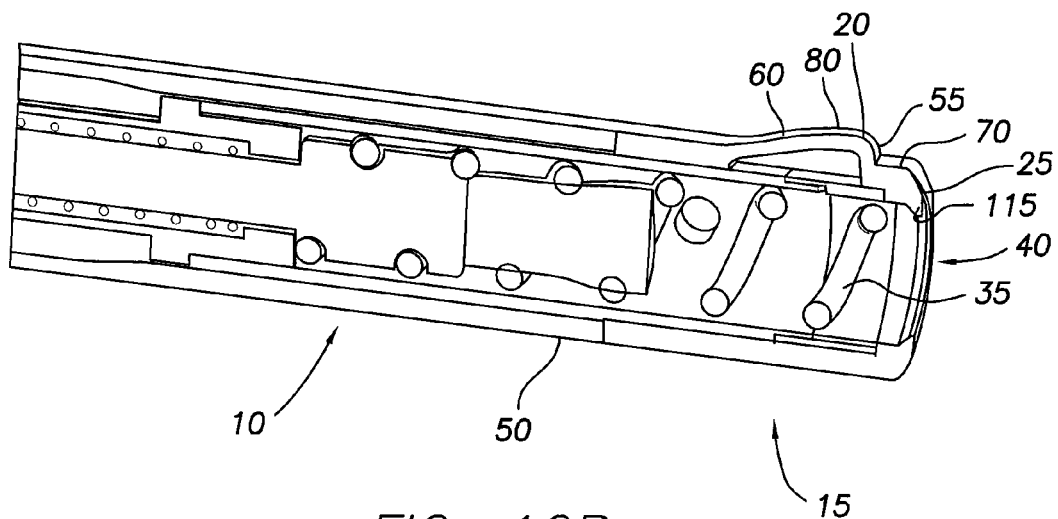
FIG. 12B is a sectional view of one embodiment of the distal end of a lead tubular body having members radially inwardly and outwardly extending from the distal end.

As illustrated in FIGS. 9A-12B, the members 20 extend radially outwardly from the distal end 15 and include a distal face 55 and a proximal face 60. As shown in FIGS. 9A-10B, the members 20 also include an outer rim 65. As shown in FIGS. 12A and 12B, the members 20 also include an outer surface 80. As shown FIGS. 11A and 11B, the members 20 also include an outer peak 120.

As indicated in FIGS. 9A-11B, each member 20 is positioned on the distal end 15 such that the member distal face 55 radially outwardly extends from the distal end face 25 of the lead tubular body 10 as a continuous uninterrupted surface to the member outer rim 65 or member outer peak 120, as the case may be. Alternatively, as depicted in FIGS. 12A-12B, each member 20 is positioned on the distal end 15 such that the member distal face 55 radially outwardly extends from the distal end 15 at a point proximally offset a small distance from the distal end face 25, thereby defining a rim or lip 70 extending circumferentially about, and generally perpendicularly to, the distal end face 25.

As can be understood from FIGS. 9A-9C, and 12A-12B, in various embodiments the tubular body outer circumferential surface 50 extends generally uniformly distally from the tubular body proximal end until reaching the proximal faces of the members 20. As can be understood from FIGS. 10A-11B, in various embodiments, the tubular body outer circumferential surface 50 extends generally uniformly distally from the tubular body proximal end until reaching a bevel 45 or lip 47 where the diameter of the lead tubular body 10 transitions to a smaller diameter to form the recess 30. The recess 30 is defined between the proximal face(s) 60 of the member(s) 20 and the bevel 45 or lip 47. The recess 30, bevel 45, and lip 47 extend about the circumference of the lead tubular body 10.

As can be understood from FIGS. 9A-12B, the members 20 are resiliently flexible and formed from a polymer material such as silicone rubber, polyurethane, SPC, or etc. As can be understood from FIGS. 9A-9C and 11A-12B, in embodiments where the members 20 do not radially extend outward from the tubular body 10 a great distance, the members 20 simply defect proximally or squish radially inward to allow the lead distal end 15 to pass through a typically sized introducer sheath. As can be understood from FIGS. 10A-10B, in embodiments where the members 20 do radially extend outward a substantial distance, the members 20 fold proximally into the recess 30 to allow the lead distal end 15 to pass through a typically sized introducer sheath.

Figure 9A:
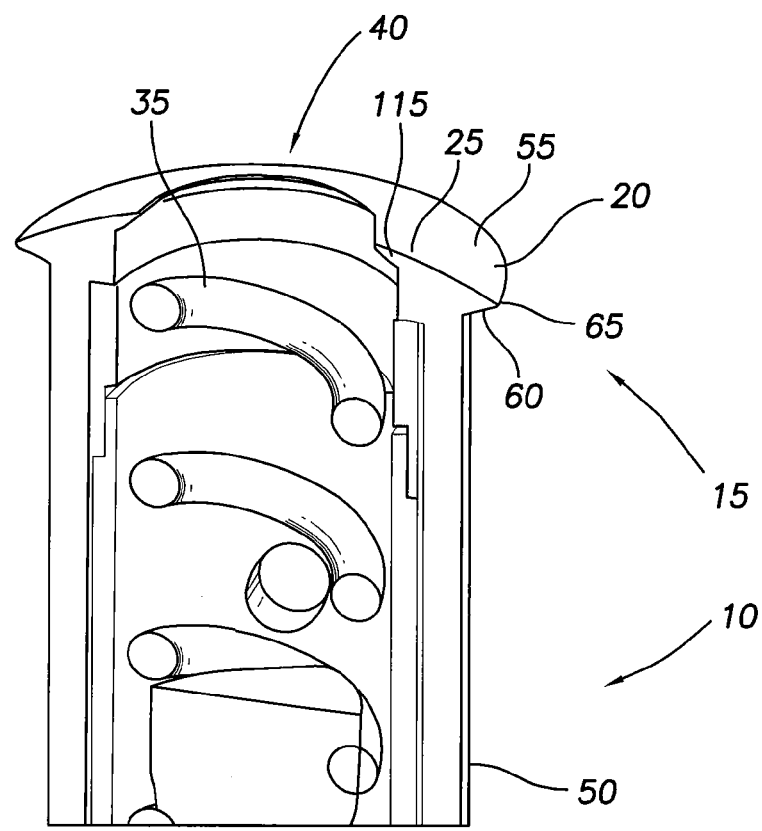
FIG. 9A is a sectional view of one embodiment of the distal end of a lead tubular body having members radially inwardly and outwardly extending from the distal end.
Figure 9B:
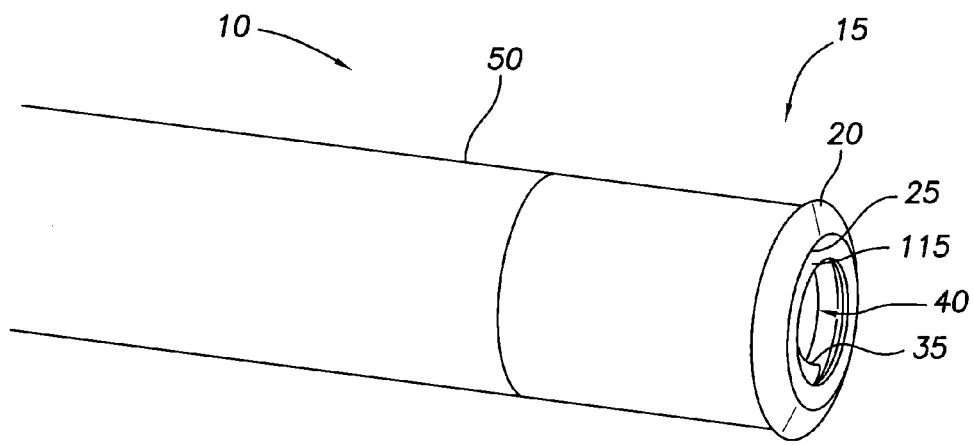
FIG. 9B is an isometric view of one embodiment of the distal end of a lead tubular body having members radially inwardly and outwardly extending from the distal end.
Figure 9C:
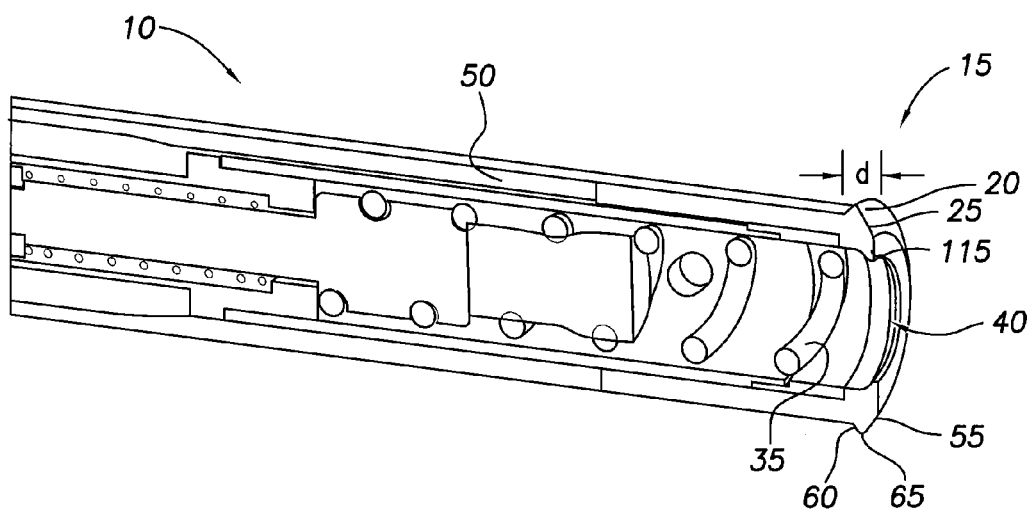
FIG. 9C is a sectional of view one embodiment of the distal end of a lead tubular body having members radially inwardly and outwardly extending from the distal end.

As can be understood from FIGS. 9C and 10B, in one embodiment, the members 20 are located a distance d of approximately 0.02 inch distal the more rigid portion of the tubular body 10. Such an arrangement allows the members 20 to freely collapse inward when the tubular body 10 is pushed through an introducer. Due to their ability to collapse inwardly, the members 20 can be made larger than they would otherwise be capable of being made.

As can be understood from FIGS. 9A-12B, once the lead distal end 15 exits the introducer distal end, the members are free to resiliently return to their radially outwardly expanded conditions. Thus, the lead tubular body 10 is advantageous because it can be deployed via a typically sized introducer sheath while providing a distal end 15 with a substantially enlarged diameter to reduce the likelihood of myocardial perforation by the lead tubular body 10 when being implanted.

FIGS. 9A-10B depict various embodiments employing generally thin members 20, which are flexibly resilient, but have solid cross-sections. As shown in FIGS. 10A and 10B, in various embodiments, the members 20 are generally rectangular and separated by V-shaped gaps 75. Each member 20 is generally of constant thickness in each dimension as it extends to its outer rim 65. As indicated in FIGS. 10A-10B, in one embodiment, the members 20 are convex in orientation such that the members 20 curve slightly proximally. As indicated in FIGS. 9A-9C, in various embodiments, the member 20 is a generally continuous radially outward extending ring or flange 20 that convexly curves from the distal end face 25 to the outer rim 65.

FIGS. 11A-12B depict various embodiments employing generally bump-like members 20 that are flexibly resilient, but may or may not have hollow cross-sections. As illustrated in FIGS. 11A and 11B, each member 20 is a nub or bump 20 with distal and proximal faces 55, 60 that curve generally equal distances to meet at a peak 120.

As depicted in FIGS. 12A and 12B, the nub or bump is hollow, but in other embodiments will have a solid cross-section. The member's distal face 55 is generally perpendicular to the outer circumferential surface 50. The member's proximal face 60 has a gradual slope leading up to the outer surface 80.

As indicated in FIGS. 9A-12B, in various embodiments, the distal face 25 extends radially inward to define a radially inwardly extending flange 115. While the flange 115 extends into the helix lumen 40, the helix 35 can displace distally/proximally as needed within the lumen 40 because the helix 35 simply deflects the flange 115, which is made of a flexible resilient polymer material such as silicone rubber, polyurethane, SPC, or etc. The surface area of the radially inwardly extending flange 115 and the surface area of the radially outwardly extending member 20 combine to substantially increase the footprint of the lead distal end 15. As a result, the likelihood of the lead distal end 15 perforating the myocardial surface is reduced. The likelihood of perforation is further reduced by the cushioning of the soft and resilient material used to form the various members 20, flanges 115 and header portion of the lead distal end 15. Also, the shape and protrusion of the various members 20 increases the resistance to penetration presented by a tubular body 10.

As shown in FIGS. 9B-9C and 12A-12B, in various other embodiments, the soft distal end 15 is made more identifiable via fluoroscopy by blending natural or dyed TiO$_2$ or barium sulfate into the silicone rubber forming the soft distal end 15. In one embodiment, the soft distal end 15 extends between approximately 0.015 inches to approximately 0.02 inches distally from the header of the lead tubular body 10.

Figure 13A:
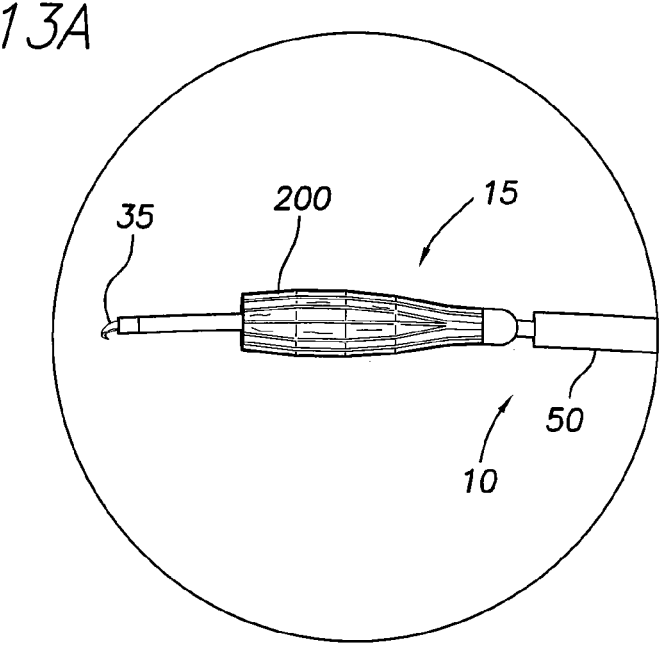
FIGS. 13A-13D are a series of side views of the lead distal end deploying from a non-expanded state (FIG. 13A), wherein the lead tubular body is capable of being routed through an introducer sheath, to an expanded state (FIG. 13D).
Figure 13B:
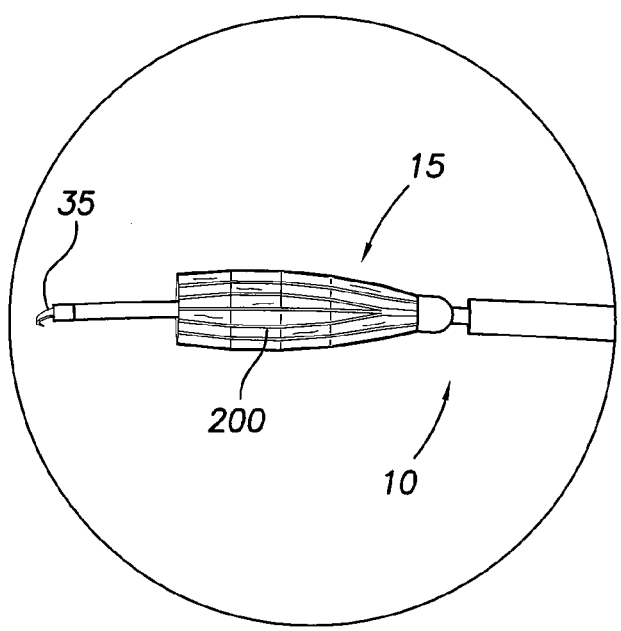
Figure 13C:
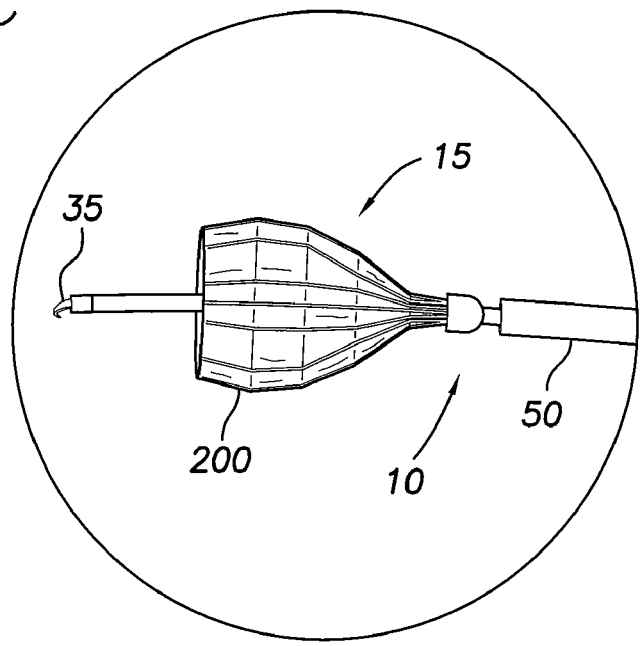
Figure 13D:
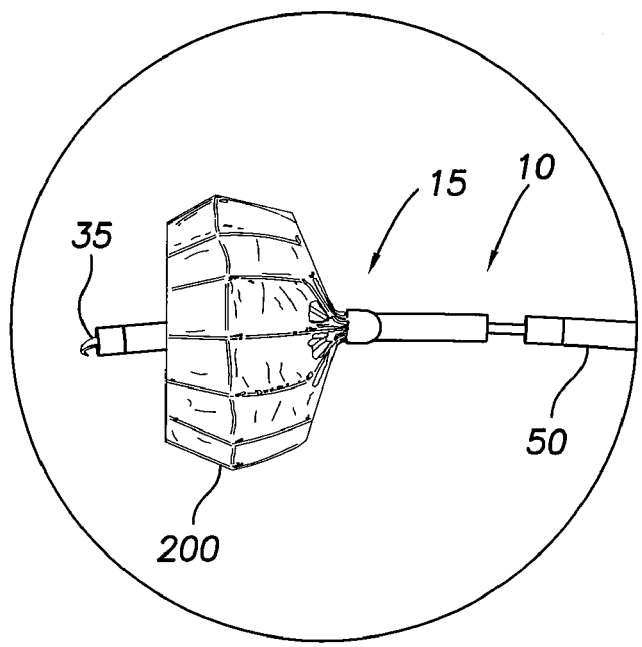
Figure 13E:
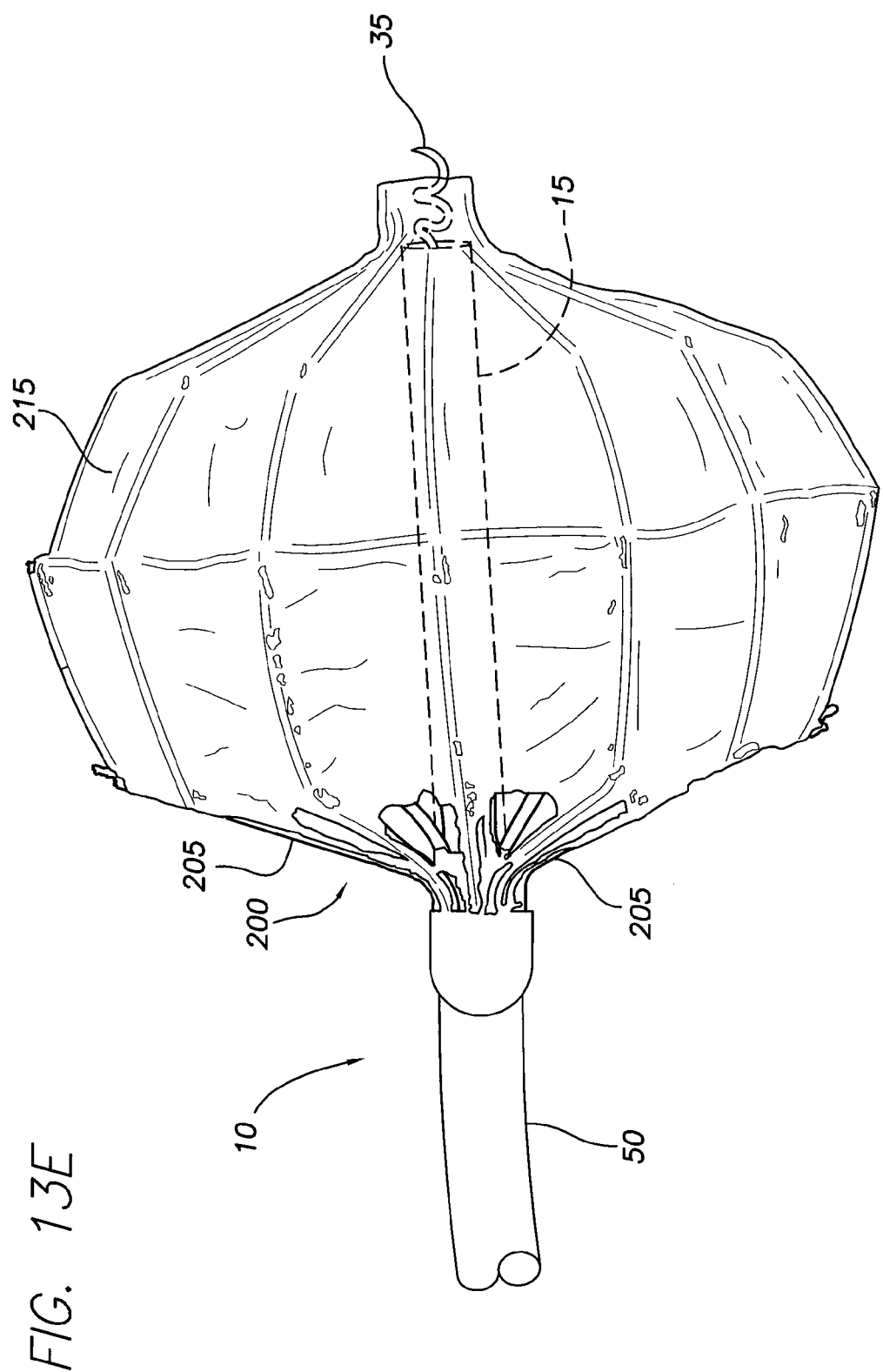
FIG. 13E is an enlarged side view of the lead distal end depicted in FIG. 13D.

For a discussion of another embodiment of the lead distal end 15, reference is made to FIGS. 13A-13D. FIGS. 13A-13D are a series of side views of the lead distal end 15 deploying from a non-expanded state (FIG. 13A), wherein the lead tubular body 10 is capable of being routed through an introducer sheath, to an expanded state (FIG. 13D). FIG. 13E is an enlarged view side view of the lead distal end 15 depicted in FIG. 13D.

As shown in FIG. 13D, in one embodiment, the lead distal end 15 includes a wire frame 200 that is biased to expand after exiting an introducer sheath. In one embodiment, the wire frame 200 is made with a shape-memory metal such as Nitinol. In one embodiment, the wire frame 200 provides a resilient spring-like function between the lead distal end 15 and the myocardial surface, thereby reducing the likelihood of myocardial surface perforation by the lead distal end 15. In one embodiment, the wire frame 200 provides a substantially increased diameter that reduces the likelihood of myocardial penetration by the lead distal end 15.

The number of wires 205 and joints 210 can have multiple configurations to optimize the spring constant, reduce the risk of wire fracture, increase footprint in contact with the myocardium, and minimize the risk of myocardial perforation. In order to limit thrombosis or unacceptable interactions with the myocardium, a cover 215 made of polytetrafluoroethylene ("PTFE") or another biocompatible material may be used to encapsulate the wire frame 200.

In one embodiment, the wire frame 200 has an expanded diameter or width dimension of between approximately five millimeters and 15 millimeters. In another embodiment, the wire frame 200 has an expanded diameter or width dimension of between approximately 15 millimeters and 32 millimeters. Such wire frames 200 when collapsed, as shown in FIG. 13A, are capable of passing through a 10F introducer sheath. The gradual deployment of the wire frame 200 from the non-expanded state (FIG. 13A) to the fully expanded state (FIG. 13D) can be seen in the series depicted in FIGS. 13A-13D.

As shown in FIG. 13E, the lead distal end 15 extends through the frame 200 from the rest of the lead tubular body 50. The helix 35 is extendable from the distal end of the frame 200.

Figure 13F:
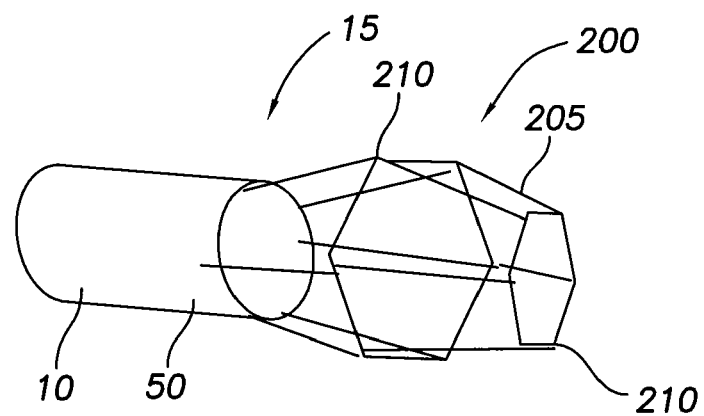
FIG. 13F is a diagrammatic isometric view of a wire frame on a tubular body distal end, wherein the wire frame is a cage in a non-deployed state.
Figure 13G:
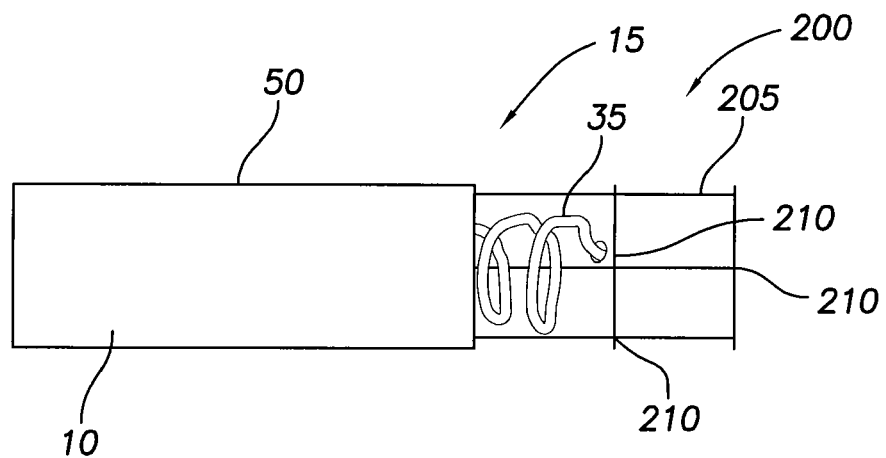
FIG. 13G is a side view of the tubular body distal end and frame depicted in FIG. 15F, wherein the frame is in a non-deployed state.
Figure 13H:
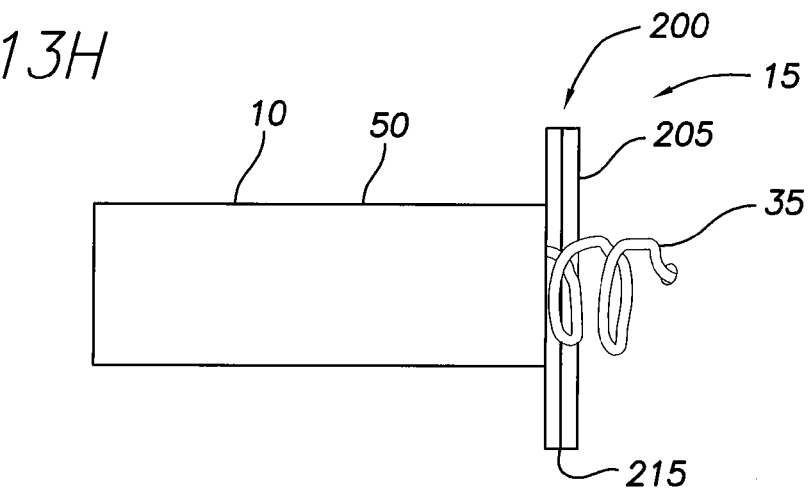
FIG. 13H is the same view as FIG. 15G, except the frame is deployed.

For a discussion regarding a wire frame configuration for use with the embodiment depicted in FIGS. 13A-13E, reference is made to FIGS. 13F-13H. FIG. 13F is a diagrammatic isometric view of a wire frame 200 on a tubular body distal end 15, wherein the wire frame 200 is a cage in a non-deployed state. FIG. 13G is a side view of the tubular body distal end 15 and frame 200 depicted in FIG. 13F, wherein the frame 200 is in a non-deployed state. FIG. 13H is the same view as FIG. 13G, except the frame 200 is deployed.

As shown in FIGS. 13F and 13G, when in a non-deployed state, the frame 200 is elongated, extending distally from the tubular body distal end 15 and having a diameter generally the same as the tubular body distal end 15. The elongated configuration of the non-deployed frame 200 allows the frame 200 to pass through the lumen of an introducer used to deliver the lead tubular body 10.

In one embodiment, the walls of the introducer lumen maintain the frame 200 in the non-deployed state as the lead distal end 15 passes through the introducer. Upon exiting the introducer lumen, the frame 200 is free to assume its deployed state, as reflected in FIG. 13H.

In its deployed state, the length of the frame 200 is substantially reduced, allowing the helix 35 to access the heart tissue for anchoring purposes once the helix 35 is distally extended from the tubular body distal end 15. In its deployed state, the width or diameter of the frame 200 is substantially increased as compared to the frame's non-deployed state. More specifically, the width or diameter of the frame 200 in the deployed state is substantially greater than the diameter of the lead distal end 15. As a result, the contact area of the lead distal end 15 is substantially increased, reducing the likelihood of cardiac perforation.

In one embodiment, the frame 200 is an assembly of wire members 205 made from an elastic or shape memory material, such as Nitinol. The wires 205 intersect with each other at joints 210 to form a frame 200 with a hexagon-shaped distal end and cross-section. The frame 200 is biased to transform from the non-deployed state (FIGS. 13F and 13G) to the deployed state (FIG. 13H).

In one embodiment, as shown in FIGS. 13A-13E, a cover 215 extends over and is stitched or otherwise attached to the frame 200. In one embodiment, the cover 215 is formed of PTFE or ePTFE.

Figure 14A:
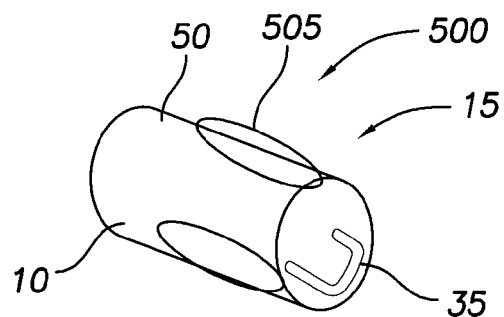
FIG. 14A is a diagrammatic isometric view of a wire frame on a tubular body distal end, wherein the wire frame employs wire rings or wings and the wire frame is in a non-deployed state.
Figure 14B:
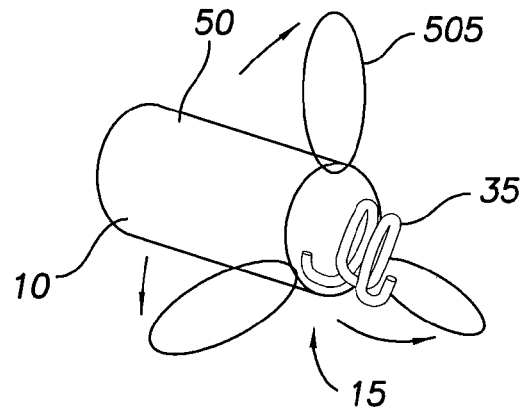
FIG. 14B is the same view as FIG. 14A, except the frame is deployed.

For a discussion of another embodiment employing an expandable wire frame concept, reference is made to FIGS. 14A-14B. FIG. 14A is a diagrammatic isometric view of a wire frame 500 on a tubular body distal end 15, wherein the wire frame 500 employs wire rings or wings 505 and the wire frame 500 is in a non-deployed state. FIG. 14B is the same view as FIG. 14A, except the frame 500 is deployed.

As shown in FIGS. 14A and 14B, in one embodiment, the wire frame 500 includes multiple wire rings or wings 505. As shown in FIG. 14A, when in a non-deployed state, the wings 505 fold back against the outer circumferential surface 50 of the lead tubular body 10. As indicated by the arrows in FIG. 14B, when expanding into the deployed state, the wings 505 unfold distally to project generally radially outward from the tubular body distal end 15. As a result, the contact area of the lead distal end 15 is substantially increased, reducing the likelihood of cardiac perforation.

In one embodiment, as the lead tubular body 10 is being delivered to the lead implantation site, the lumen walls of the introducer maintain the wings 505 in the non-deployed state depicted in FIG. 14A. Distally extending the distal end 15 from the introducer lumen allows the wings 505 to expand into the deployed state depicted in FIG. 14B. Once the wings 505 are fully deployed, the helix 35 can be distally extended, as shown in FIG. 14B.

In one embodiment, the wings 505 are made from a shape memory material, such as Nitinol. In one embodiment, the frame 500 is formed of one, two, three or more wings 505.

Although the present invention has been described with reference to preferred embodiments, persons skilled in the art will recognize that changes may be made in form and detail without departing from the spirit and scope of the invention.

What is claimed is:

1. An implantable cardiac electrotherapy lead comprising:
   a tubular body including a lumen opening to a distal end of the lead;
   a first soft resilient member extending radially outward from the distal end of the lead relative to a longitudinal axis of the lumen of the tubular body; and
   a fixation mechanism contained within the lumen when in a retracted position, the fixation mechanism adapted to be extendable beyond the lumen opening for fixing the lead distal end to a myocardial surface.

2. The lead of claim 1, wherein the distal end further includes a distal end face, the first member includes a distal face, and the distal face of the first member extends as a generally uniform and uninterrupted surface from the distal face of the distal end.

3. The lead of claim 2, wherein the distal face of the first member is convexly curved.

4. The lead of claim 2, wherein the distal face of the first member is concavely curved.

5. The lead of claim 1, wherein the distal end further includes a distal end face, the first member includes a distal face, and the distal face of the first member is offset proximally from the distal end face of the distal end, thereby defining a lip.

6. The lead of claim 1, wherein the first member is a disk eccentric with a lumen of the distal end.

7. The lead of claim 1, wherein the first member is a disk concentric with a lumen of the distal end.

8. The lead of claim 1, wherein the first member has a radial length, a width transverse and similar to the radial length, and a thickness substantially less than the length or width.

9. The lead of claim 8, wherein the thickness tapers traveling along the radial length towards an outer rim of the first member.

10. The lead of claim 1, wherein the first member is bump or nub-like in shape.

11. The lead of claim 10, wherein the first member is bump or nub-like in shape and is hollow.

12. The lead of claim 1, wherein the first member has a radial length, a width transverse to and substantially smaller than the radial length, and a thickness substantially less than the length or width.

13. The lead of claim 1, wherein the tubular body further includes a recess defined in a circumference of the tubular body proximal to the first member.

14. The lead of claim 1, wherein the tubular body further includes a pocket defined in a circumference of the tubular body proximal to the first member and generally similar in shape to the first member.

15. The lead of claim 1, wherein the distal end further includes a soft resilient second member extending from the distal end radially inward relative to the longitudinal axis of the tubular body.

16. The lead of claim 1, wherein the first soft resilient member is configured to reduce a likelihood of tissue penetration by the distal end as the lead is implanted in a patient.

17. The lead of claim 1, wherein the lumen is configured to pass the fixation mechanism and the first soft resilient member is configured to reduce a likelihood of undesired tissue penetration by the fixation mechanism as the lead is implanted in a patient.

18. The lead of claim 1, wherein the first soft resilient member defines at least part of a distal end face of the distal end.

19. The lead of claim 1, wherein the distal end includes a distal end face and the first soft resilient member extends radially outward substantially parallel to the distal end face.

20. The lead of claim 1, wherein the distal end includes a radially inwardly extending flange, wherein a surface area of the radially inwardly extending flange and a surface area of the radially outwardly extending member combine to increase a footprint of the lead distal end.

21. The lead of claim 20, wherein the radially inwardly extending flange comprises a flexible resilient material.

22. The lead of claim 20, wherein the radially inwardly extending flange extends radially inwardly from a distal end face of the distal end.

23. The lead of claim 22, wherein first soft resilient member extends radially outward from the distal end face of the distal end, whereby the radially inwardly extending flange and the first soft resilient member increase a surface area of the distal end.

24. The lead of claim 1, wherein the first soft resilient member extends radially outward in response to exposure to an activating material.

25. The lead of claim 24, wherein the activating material is a biological fluid.

26. The lead of claim 24, wherein the activating material is a steroid.

27. The lead of claim 24, wherein the first soft resilient member comprises a swellable material such that the member extends radially outward in response to exposure to the activating material by swelling.

28. The lead of claim 1, further comprising a dissolvable member, wherein the first soft resilient member comprises a preformed material having a preformed extended state, the dissolvable member constraining the preformed material of the first soft resilient member in a non-extended state, the first soft resilient member extending radially outward only once the dissolvable member is sufficiently dissolved to allow the preformed material of the first soft resilient member to assume the preformed extended state.

29. The lead of claim 28, wherein the dissolvable member is dissolvable by a biological fluid.

30. An implantable cardiac electrotherapy lead comprising:
a tubular body including a lumen opening to a distal end;
a member extendable radially outward from the distal end relative to a longitudinal axis of the lumen of the tubular body; and
a fixation mechanism contained within the lumen when in a retracted position, the fixation mechanism adapted to be extendable beyond the lumen opening for fixing the lead distal end to a myocardial surface.

31. The lead of claim 30, wherein the member is formed of a soft resilient material.

32. The lead of claim 30, wherein the member includes a wire frame biased to radially expand upon leaving the confines of an introducer sheath.

33. The lead of claim 30, wherein the member includes a wire wing biased to pivot from a proximal non-deployed state to a radially expanded deployed state.

34. The lead of claim 30, wherein the first soft resilient member is configured to reduce a likelihood of tissue penetration by the distal end as the lead is implanted in a patient.

35. The lead of claim 30, wherein the lumen is configured to pass a fixation mechanism and the first soft resilient member is configured to reduce a likelihood of undesired tissue penetration by the fixation mechanism as the lead is implanted in a patient.

36. The lead of claim 30, further comprising a dissolvable member, wherein the first soft resilient member comprises a preformed material having a preformed extended state, the dissolvable member constraining the preformed material of the first soft resilient member in a non-extended state, the first soft resilient member extending radially outward only once the dissolvable member is sufficiently dissolved to allow the preformed material of the first soft resilient member to assume the preformed extended state.

37. The lead of claim 36, wherein the dissolvable member is dissolvable by a biological fluid.

* * * * *